United States Patent [19]

Lang et al.

[11] Patent Number: 4,483,983
[45] Date of Patent: Nov. 20, 1984

[54] SUBSTITUTED DERIVATIVES OF THIAMORPHOLINONE

[75] Inventors: Gérard Lang, Epinay Sur Seine; Jean Maignan, Tremblay Les Gonesse; Jean-Luc Leveque, Paris; Laurent Rasseneur, Thorigny, all of France

[73] Assignee: Societe Anonyme dite: L'Oreal, Paris, France

[21] Appl. No.: 484,605

[22] Filed: Apr. 13, 1983

[30] Foreign Application Priority Data

Apr. 15, 1982 [FR] France ................ 82 06498

[51] Int. Cl.³ .................... C07D 279/12; A61K 7/40; A61K 31/54
[52] U.S. Cl. ................................. 544/58.2
[58] Field of Search ........................ 544/58.2

[56] References Cited

FOREIGN PATENT DOCUMENTS 1327331 8/1973 United Kingdom ............... 544/58.2

OTHER PUBLICATIONS

Basic Principles of Organic Chemistry, John D. Roberts and Marjorie C. Caserio, 1965, p. 563.

Primary Examiner—Henry R. Jiles
Assistant Examiner—J. G. Mullins
Attorney, Agent, or Firm—Cushman, Darby & Cushman

[57] ABSTRACT

A substituted derivative of thiamorpholinone, for use in the cosmetic and pharmaceutical field, has the formula

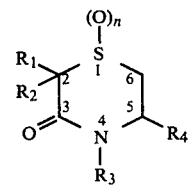

wherein n is 0 or 1; $R_1$ and $R_2$ each independently represent hydrogen or lower alkyl and $R_3$ represents hydrogen, mono or polyhydroxyalkyl containing 2–16 carbon atoms, carbamylalkyl, carboxyalkyl or alkoxycarbonylalkyl. When $R_3$ represents hydrogen, $R_4$ represents $-CO_2R_5$ wherein $R_5$ is alkyl having 3–18 carbon atoms, optionally interrupted by one or more heteroatoms, or mono or polyhydroxyalkyl having 2–18 carbon atoms. When $R_3$ represents mono or polyhydroxyalkyl, carbamylalkyl, carboxyalkyl or alkoxycarbonylalkyl, $R_4$ represents hydrogen or lower alkyl.

5 Claims, No Drawings

SUBSTITUTED DERIVATIVES OF THIAMORPHOLINONE

The present invention relates to new substituted derivatives of thiamorpholinone, to the sulfoxides of these derivatives, as well as to a process for their preparation.

These new derivatives of thiamorpholinone are quite particularly suitable for use in the cosmetic and dermatology field; they exhibit excellent hydrating properties as well as emollient, softening and suppleness characteristics.

More particularly these derivatives find a cosmetic use in the field of sunscreen and capillary products.

The present invention thus relates to, as new industrial products, the substituted derivatives of thiamorpholinone having the following general formula:

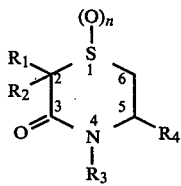

wherein n is 0 or 1, $R_1$ and $R_2$, each independently, represent hydrogen or lower alkyl having 1–4 carbon atoms, and $R_3$ represents hydrogen, mono- or polyhydroxy alkyl having 2–16 carbon atoms, carbamylalkyl, carboxyalkyl or alkoxycarbonylalkyl, (i) when $R_3$ represents hydrogen, $R_4$ represents $-CO_2R_5$ wherein $R_5$ is alkyl having from 3 to 18 carbon atoms, optionally interrupted by one or more heteroatoms, or a mono- or polyhydroxyalkyl having from 2–18 carbon atoms, (ii) when $R_3$ represents mono- or polyhydroxyalkyl, carbamylalkyl, carboxyalkyl or alkoxy carbonylalkyl, $R_4$ represents hydrogen or a lower alkyl having from 1–4 carbon atoms.

When $R_1$ and $R_2$ represent lower alkyl they can be methyl, ethyl, propyl, isopropyl or butyl.

When $R_3$ represents mono- or polyhydroxyalkyl it can be, for example, 2-hydroxyethyl, 2-hydroxypropyl, or 2,3-dihydroxypropyl.

When $R_3$ represents carbamylalkyl, carboxyalkyl or alkoxycarbonyl alkyl, the alkyl moiety of each, branched or not, has preferably from 1–17 carbon atoms and the alkoxy moiety has from 1–3 carbon atoms.

When $R_5$ represents alkyl having from 3 to 18 carbon atoms, it can be, for example, propyl, butyl, pentyl, hexyl, 2-ethyl hexyl, octyl, decyl, dodecyl, tetradecyl or hexadecyl.

Representative compounds which correspond to Formula I, above, include, in particular, the following:

(1) 4-(2-hydroxy ethyl)-3-thiamorpholinone, (2) 4-(2-hydroxyethyl)-1-oxo-3-thiamorpholinone, (3) 4-(2-hydroxypropyl)-3-thiamorpholinone, (4) 4-(2,3-dihydroxypropyl)-3-thiamorpholinone, (5) 3-thiamorpholinone-5-n-octylcarboxylate, (6) 3-thiamorpholinone-5-n-decyl carboxylate, (7) 3-thiamorpholinone-5-n-dodecyl carboxylate, (8) 3-thiamorpholinone-5-(2-ethyl)hexyl carboxylate, (9) 3-thiamorpholinone-5-n-tetradecyl carboxylate,

(10) 3-thiamorpholinone-5-n-hexadecyl carboxylate,

(11) 3-thiamorpholinone-5-(2-hydroxy)propyl carboxylate,

(12) 3-thiamorpholinone-5-(2,3-dihydroxy)propyl carboxylate,

(13) 4-(ethoxy carbonylmethyl)-3-thiamorpholinone,

(14) 4-(methoxy carbonylmethyl)-3-thiamorpholinone,

(15) 4-(2-ethoxycarbonylethyl)-3-thiamorpholinone,

(16) 4-(1-ethoxycarbonylethyl)-3-thiamorpholinone,

(17) 4-(carboxymethyl)-3-thiamorpholinone,

(18) 4-(2-carboxyethyl)-3-thiamorpholinone,

(19) 4-(1-carboxyethyl)-3-thiamorpholinone, and

(20) 4-(carbamylmethyl)-3-thiamorpholinone.

The present invention also relates to a process for preparing the compounds of Formula I.

When, in the compounds of Formula I, $R_3=H$ and $R_4=CO_2R_5$, these compounds are prepared by esterification of corresponding thiamorpholinone carboxylic acids, optionally mono- or di-substituted in the 2 position.

The thiamorpholinone carboxylic acids of formula (3), below, can themselves be obtained according to one of the two methods represented by the following reaction scheme:

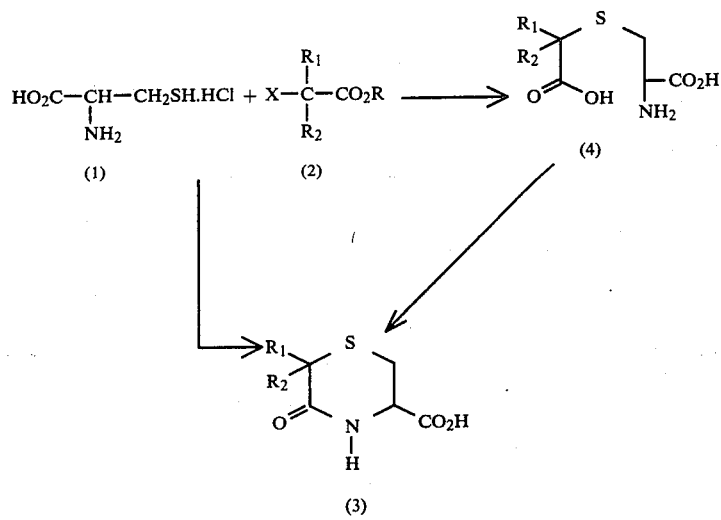

The value of the various R's is alkyl having 1-3 carbon atoms.

According to a first method, there is reacted in an alkaline medium (pH≃9) cysteine hydrochloride (1) with one equivalent of an α-halogenated ester (2), optionally mono- or di-substituted, in a polar hydroalcoholic medium, preferably at a temperature near 50° C., this temperature being maintained for a period of about 10 to 20 hours.

The resulting mixture is acidified to pH≃1 and then concentrated under reduced pressure, the resulting thiamorpholinone carboxylic acid (3) being extracted with chloroform and then purified by recrystallization.

The second method of producing the thiamorpholinone carboxylic acids (3) uses, as the starting product, an S-(2-carboxyalkyl) cysteine (4), optionally mono- or di-substituted, which is cyclized by heating at an elevated temperature of about 170° C. in solution in orthodichlorobenzene until the theoretical quantity of water is removed.

The S-(2-carboxyalkyl) cysteines (4), optionally substituted, are known compounds which have been described in French patents Nos. 1.472.021 and 69.01404.

The compounds in which $R_3$ represents hydroxyalkyl, carbamylalkyl carboxyalkyl or alkoxycarbonylalkyl are obtained in accordance with the following reaction scheme:

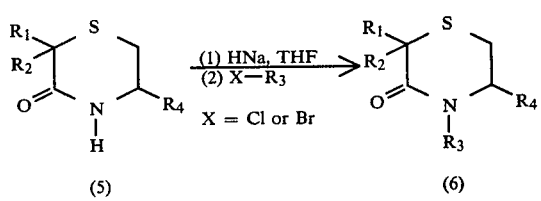

This method comprises treating with an alkylating agent, X—$R_3$, the sodium salt (obtained by the action of sodium hydride in tetrahydrofuran) of a thiamorpholinone (5), optionally substituted.

Generally, the reaction is carried out at a temperature of about 50° C. under an inert atmosphere.

The compounds of Formula I in which $R_4$=H or alkyl and $R_3$ represents mono- or polyhydroxyalkyl, carbamylalkyl, carboxyalkyl or alkoxycarbonylalkyl can also be obtained in accordance with the following reaction scheme:

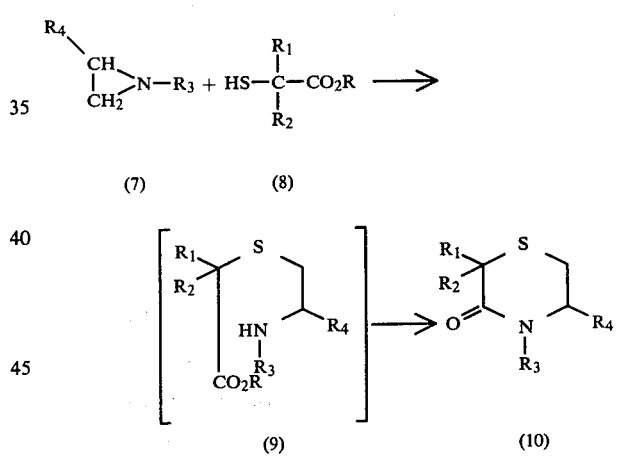

wherein the value of the various R's is alkyl containing 1-3 carbon atoms.

This method comprises reacting an aziridine (7), optionally substituted, with an α-mercapto ester (8) in a polar solvent such as methanol or ethanol at ambient temperature. After the disappearance of the initial mercaptan reactant, the mixture is brought to the boil so as to effect or terminate the cyclization reaction. The solvent is then removed by evaporation under a vacuum and the resulting N-substituted thiamorpholinone (10) is purified either by distillation or by recrystallization in an appropriate solvent.

The compounds of Formula I wherein n=1, or sulfoxides, are prepared following known methods by reacting at 0° C. one equivalent of $H_2O_2$ with the thiamorpholinone of Formula I wherein n=0 in the presence of an organic acid such as acetic or formic acid.

The following non-limiting examples illustrate the present invention.

EXAMPLE 1

4-(2-hydroxyethyl)-3-thiamorpholinone

(Compound 1)

To a stirred solution, at ambient temperature, of 120 g of ethyl thioglycolate (1 mole) in 300 cm³ of absolute ethanol, placed under an inert atmosphere, there is slowly added a solution of 87 g (1 mole) of N-(2-hydroxyethyl) aziridine diluted in 100 cm³ of ethanol. The reaction is exothermic and the temperature of the reaction mixture is maintained at a temperature lower than 50° C. About one-half hour after the end of the introduction, the solution is held under reflux for 6 hours.

The ethanol is then eliminated and the liquid obtained is distilled under reduced pressure.

B.P. (0.1–0.3 mm) = 165°–170° C.

4-(2-hydroxyethyl)-3-thiamorpholinone is a hygroscopic, viscous, light yellow liquid, the elemental analysis of which under the hydrated form is as follows:

Analysis: $C_6H_{11}NO_2S.0.25H_2O$ Calc: C 43.48; H 6.99; N 8.45; O 21.73; S 19.35; Theory: 43.37; 6.96; 8.44; 21.37; 19.36.

EXAMPLE 2

4-(2-hydroxyethyl)-1-oxo-3-thiamorpholinone

(Compound 2)

This sulfoxide is prepared by reacting for a week one equivalent of $H_2O_2$ on 4-(2-hydroxyethyl)-3-thiamorpholinone (obtained in Example 1) solubilized at 0° C. in a mixture of acetic acid and acetic anhydride. After concentrating the mixture, the resulting liquid is dissolved in a minimum of an isopropyl ether isopropyl alcohol mixture. Starting with this solution the temperature of which is adjusted to −25° C., white crystals whose melting point is 45° C. are isolated.

Analysis: $C_6H_{11}NO_3S$ Calc: C 40.66; H 6.26; N 7.80; S 18.08; Theory: 40.73; 6.28; 7.73; 18.16.

EXAMPLE 3

4(2,3-dihydroxypropyl)-3-thiamorpholinone

(Compound 4)

To the sodium salt of 3-thiamorpholinone, prepared by the reaction of the latter with sodium hydride in tetrahydrofuran brought to the boil, there are added after cooling, 1.1 equivalents of epichlorohydrin. The reaction mixture is then held for 4 hours at 50° C. After cooling, the reaction mixture is filtered, concentrated and deposited on a silica gel column.

The 4-(2,3-epoxypropyl)-3-thiamorpholinone is eluted with a 1:1 ethylacetate-methanol mixture. After concentration of the elution phases and verification of the structure, the epoxide is hydrolyzed with a few drops of HCl. After verification in C.C.M. of the total transformation of the 4-(2,3-epoxypropyl)-3-hiamorpholinone into 4-(2,3-dihydroxypropyl)-3-thiamorpholinone, the solution is concentrated under reduced pressure. The resulting yellow colored liquid is dried in a dessicator and the anticipated structure is confirmed by mass spectograph: molecular ion m/e:191 (base peak m/e:102).

EXAMPLE 4

3-thiamorpholinone-5 n-octyl carboxylate

(Compound 5)

(a) Preparation of 3-thiamorpholinone-5-carboxylic acid.

A suspension of 179.5 g of S-carboxymethyl cysteine (1 mole) in 500 cm³ of o-dichlorobenzene, vigorously stirred under an inert atmosphere, is held at 170° C. The temperature of the oil bath is progressively elevated until the azeotropic o-dichlorobenzene/water mixture distills. This mixture is recovered in a test tube and gives two phases at ambient temperature. The heating is maintained until the volume of the upper phase corresponds to the theoretical quantity of water, i.e. 18 cm³.

Then the reaction mixture is cooled and the resulting highly colored solid is filtered, washed with hexane and then dried. This resulting colored solid is then dissolved in 4.5 liters of methanol in the presence of animal charcoal. The mixture is filtered and the filtrate is then concentrated to about 1.5 liters, after which it is cooled to 0° C. On filtration, there are isolated, after drying, 115 g of beige crystals whose melting point is 188° C.

Analysis: $C_5H_7NO_3S$ Calc: C 37.26; H 4.38; N 8.69; O 29.78; S 19.89; Theory: 37.24; 4.33; 8.76; 29.95; 19.88.

(b) Preparation of the octylester of 3-thiamorpholinone-5-carboxylic acid.

Method A—Initially there is prepared the sodium salt of 3-thiamorpholinone-5-carboxylic acid which is obtained in accordance with Example 4(a) by bringing a mixture of 3.2 g of this acid (0.02 mole) and 1 g of sodium carbonate (0.01 mole) in 20 cm³ of dimethylformamide (DMF) to a temperature of about 70° C.

After a few minutes the mixture is homogeneous and 3.8 g of n-octylbromide (0.02 mole) are added. Then the temperature of the reaction mixture is raised to 120° C. for one hour. After cooling, the sodium bromide is filtered off and the solution is concentrated under reduced pressure. The resulting liquid is stirred into a 95:5 mixture of methylene chloride—ethylacetate in the presence of silica gel so as to eliminate the colored impurities. After filtration, the solution is concentrated under vacuum and the desired product crystallizes, yielding 5 g of a pasty solid whose melting point is 45° C.

Analysis: $C_{13}H_{23}NO_3S$ Calculated: C 57.11; H 8.48; N 5.12; S 11.73; Theoretical: 57.10; 8.43; 5.12; 11.79.

Method B—The temperature of a stirred mixture of 9 g of S-carboxymethyl cysteine (0.05 mole) in an excess of n-octanol (0.1 mole) under an inert atmosphere is raised to 170° C. for 2 hours.

After cooling, the mixture is dissolved in a minimum of toluene and the solution is deposited on a silica gel column which is then eluted using a 95:5 methylene chloride-ethylacetate mixture.

After concentration of the elution phases the desired ester is obtained, this ester having characteristics which are identical to those of the ester obtained in accordance with Method A, above.

EXAMPLES 5–9

In accordance with the same operating procedures as those in Method B of Example 4(b) and by using the same amounts of reactants, the following esters are also obtained:

EXAMPLE 5

3-thiamorpholinone-5-n-decyl carboxylate (Compound 6)

Starting with n-decyl alcohol, pasty beige crystals are obtained whose melting point is 48° C.

Analysis: $C_{15}H_{27}NO_3S$ Calculated: C 59.77; H 9.03; N 4.65; S 10.64; Theoretical: 59.90; 9.01; 4.60; 10.66.

EXAMPLE 6

3-thiamorpholinone-5-n-dodecyl carboxylate (Compound 7)

Starting with n-dodecanol, an amorphous beige solid is obtained whose melting point is 50° C.

Analysis: $C_{17}H_{31}NO_3S$ Calculated: C 61.97; H 9.48; N 4.25; S 9.73; Theoretical: 61.75; 9.48; 4.28; 9.87.

EXAMPLE 7

3-thiamorpholinone-5-(2-ethyl)hexyl carboxylate (Compound 8)

Starting with 2-ethyl hexanol, a colorless liquid is obtained which is then purified by chromatography on silica gel.

Analysis: $C_{13}H_{22}NO_3S$ Calculated: C 57.11; H 8.43; N 5.12; S 11.73; Theoretical: 56.96; 8.53; 4.99; 11.68.

EXAMPLE 8

3-thiamorpholinone-5-n-tetradecyl carboxylate (Compound 9)

Starting with n-tetradecanol, crystals are obtained which are then purified initially by chromatography on silica gel and then by recrystallization in petroleum ether.

The expected ester is provided in the form of a beige solid whose melting point is 66° C.

Analysis: $C_{19}H_{35}NO_3S$ Calculated: C 63.92; H 9.87; N 3.92; S 8.97; Theoretical: 64.04; 9.86; 3.89; 8.94.

EXAMPLE 9

3-thiamorpholinone-5-n-hexadecyl carboxylate (Compound 10)

Starting with n-hexadecanol, the expected ester is obtained which is then purified by chromatography on silica gel. After concentration of the elution phases, the ester is provided in the form of a white powder whose melting point is 75° C.

Analysis: $C_{21}H_{39}NO_3S$ Calculated: C 65.40; H 10.19; N 3.65; S 8.31; Theoretical: 65.50; 10.12; 3.59; 8.29.

EXAMPLE 10

3-thiamorpholinone-5-(2,3-dihydroxy)propyl carboxylate (Compound 12)

This product is prepared in accordance with Method A of Example 4(b).

The sodium salt of 3-thiamorpholinone-5-carboxylic acid in DMF is treated with one equivalent of 3-chloro-1,2-propanediol for 8 hours at 120° C.

After cooling, the insolubles are filtered off and the filtrate is concentrated under reduced pressure. The resulting liquid is treated with animal charcoal in methanol. After filtration, the methanolic phase is concentrated, the desired product being then purified by passage through silica gel and eluted with a 9:1 ethyl acetate: methanol mixture.

After concentration of the elution phases a very viscous liquid is obtained having a yellow color and whose R.M.N. and mass spectra correspond to the expected structure (molecular ion at m/e:235, base peak at m/e:116).

EXAMPLE 11

4-(ethoxycarbonylmethyl)-3-thiamorpholinone (Compound 13)

To a solution of 5 g of 3-thiamorpholinone in 100 cm³ of anhydrous tetrahydrofuran, stirred out of contact with the humidity of the air, there are added 1.1 equivalents of sodium hydride, the resulting mixture being held at reflux for one hour.

There are then slowly added, at ambient temperature, 1.1 equivalents of ethyl chloroacetate. The reaction mixture is then brought to 50° C. for one hour, then the mineral salts are filtered off, and washed with THF. The filtrate is concentrated under reduced pressure and the residue is then dissolved in a minimum of methylene chloride to remove any remaining traces of sodium chloride. The methylene chloride phase is filtered and the solvent rectified under vacuum.

The 4-(ethoxycarbonylmethyl)-3-thiamorpholinone is a yellow colored liquid at ambient temperature.

Analysis: $C_8H_{13}NO_3S$, ¼$H_2O$ Calculated: C 46.27; H 6.50; N 6.75; O 25.06; S 15.42; Theoretical: 46.38; 6.43; 6.81; 25.09; 15.46.

EXAMPLE 12

4-(carboxymethyl)-3-thiamorpholinone (Compound 17)

To a solution of 2 g of the ester of Example 11 in 50 cm³ of ethanol, there are added 1.1 equivalents of alcoholic potash.

The mixture is held for one hour under agitation at the boil. After cooling, the crystallized potassium salt is filtered, washed with a little pure ethanol and dried.

One thus obtains 1.68 g of salt that is then stirred in suspension in isopropanol and to which is added the stoichiometric amount of HCl acid in solution in isopropanol.

After one hour, the mixture is filtered. The filtrate is then concentrated under reduced pressure. The expected acid is dissolved hot in 1,2-dichloroethane. Then the solution is filtered in order to remove any traces of potassium chloride and the solvent is rectified under reduced pressure, yielding 1.30 g of 4-(carboxymethyl)-3-thiamorpholinone in the form of beige colored crystals whose melting point is 138° C.

Analysis: $C_6H_9NO_3S$ Calculated: C 41.14; H 5.14; N 8.00; O 27.43; S 18.29; Theoretical: 41.11; 5.15; 8.04; 27.50; 18.26.

EXAMPLE 13

4-(carbamylmethyl)-3-thiamorpholinone (Compound 20)

The reaction is carried out as in the case of the preparation of 4-(ethoxycarbonylmethyl)-3-thiamorpholinone (Example 11) by replacing ethyl chloroacetate with chloroacetamide.

At the end of the reaction the anticipated product is purified initially by crystallization in ethyl acetate and then by washing the expected crystals with acetone.

The 4-(carbamylmethyl)-3-thiamorpholinone is a white solid whose melting point is 145° C.

Analysis: $C_6H_{10}N_2O_2S$ Calculated: C 41.38; H 5.75; N 16.09; O 18.36; S 18.40; Theoretical: 41.40; 5.81; 16.11; 18.50; 18.33.

What is claimed is:

1. A substituted derivative of thiamorpholinone having the formula

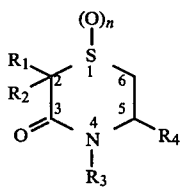

wherein n is 0 or 1, $R_1$ and $R_2$, each independently, represents hydrogen or lower alkyl having 1–4 carbon atoms, and $R_3$ represents hydrogen, mono- or polyhydroxyalkyl having 2–16 carbon atoms, carbamylalkyl, carboxyalkyl or alkoxycarbonylalkyl wherein the alkyl moieties, branched or straight chain, have 1–17 carbon atoms and the alkoxy moiety has 1–3 carbon atoms, (i) when $R_3$ represents hydrogen, $R_4$ represents —$CO_2R_5$ wherein $R_5$ represents alkyl having 3–18 carbon atoms, or a mono- or polyhydroxyalkyl having 2–18 carbon atoms, (ii) when $R_3$ represents mono- or polyhydroxy alkyl, carbamyl alkyl, carboxy alkyl or alkoxycarbonyl alkyl, $R_4$ represents hydrogen or lower alkyl having 1–4 carbon atoms.

2. The substituted derivative of claim 1 wherein $R_1$ and $R_2$ each independently represent methyl, ethyl, propyl, isopropyl or butyl.

3. The substituted derivative of claim 1 wherein $R_3$ represents 2-hydroxyethyl, 2-hydroxy propyl or 2,3-dihydroxypropyl.

4. The substituted derivative of claim 1 wherein $R_5$ represents propyl, butyl, pentyl, hexyl, 2-ethylhexyl, octyl, decyl, dodecyl, tetradecyl or hexadecyl.

5. The substituted derivative of claim 1 selected from the group consisting of
   (1) 4-(2-hydroxyethyl)-3-thiamorpholinone,
   (2) 4-(2-hydroxyethyl)-1-oxo-3-thiamorpholinone,
   (3) 4-(2-hydroxypropyl)-3-thiamorpholinone,
   (4) 4-(2,3-dihydroxypropyl)-3-thiamorpholinone,
   (5) 3-thiamorpholinone-5-n-octyl carboxylate,
   (6) 3-thiamorpholinone-5-n-decyl carboxylate,
   (7) 3-thiamorpholinone-5-n-dodecyl carboxylate,
   (8) 3-thiamorpholinone-5-(2-ethyl)hexyl carboxylate,
   (9) 3-thiamorpholinone-5-n-tetradecyl carboxylate,
   (10) 3-thiamorpholinone-5-hexadecyl carboxylate,
   (11) 3-thiamorpholinone-5-(2-hydroxy)propyl carboxylate,
   (12) 3-thiamorpholinone-5-(2,3-dihydroxy)propyl carboxylate,
   (13) 4-(ethoxycarbonylmethyl)-3-thiamorpholinone,
   (14) 4-(methoxycarbonylmethyl)-3-thiamorpholinone,
   (15) 4-(2-ethoxycarbonylethyl)-3-thiamorpholinone,
   (16) 4-(1-ethoxycarbonyl ethyl)-3-thiamorpholinone,
   (17) 4-(carboxymethyl)-3-thiamorpholinone,
   (18) 4-(2-carboxyethyl)-3-thiamorpholinone,
   (19) 4-(1-carboxyethyl)-3-thiamorpholinone, and
   (20) 4-(carbamylmethyl)-3-thiamorpholinone.

* * * * *